Figure 1:
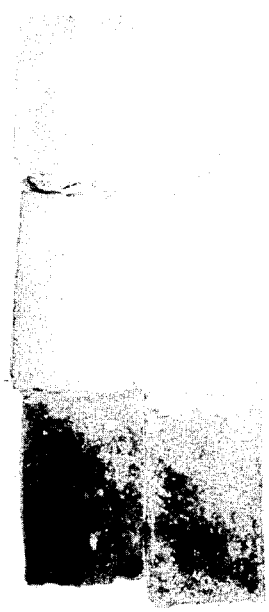
Figure 2:
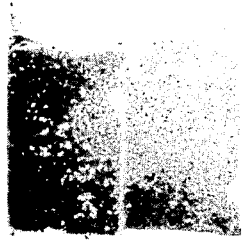

United States Patent [19]

Eoga

[11] Patent Number: 4,701,223

[45] Date of Patent: Oct. 20, 1987

[54] LIQUID DENTURE CLEANSER COMPOSITION AND METHOD OF APPLICATION

[75] Inventor: Anthony B. J. Eoga, Boonton, N.J.

[73] Assignee: Warner-Lambert Company, Morris Plains, N.J.

[21] Appl. No.: 856,715

[22] Filed: Apr. 28, 1986

Related U.S. Application Data

[63] Continuation-in-part of Ser. No. 684,818, Dec. 20, 1984, abandoned.

[51] Int. Cl.$^4$ ................................................. C11D 1/02
[52] U.S. Cl. ........................................ 134/2; 134/42; 252/531; 252/539; 252/546; 252/550; 252/554; 252/558; 252/DIG. 11; 424/52; 424/54; 424/56
[58] Field of Search ............... 134/2, 42; 252/531, 252/535, 539, 546, 550, 554, 558, DIG. 11; 424/52, 54, 56

[56] References Cited

U.S. PATENT DOCUMENTS

| | | | |
|---|---|---|---|
| 3,822,212 | 7/1974 | Bryant et al. | 252/136 |
| 3,839,213 | 10/1974 | Hill | 252/174.25 |
| 3,957,967 | 5/1976 | L'Orange | 424/48 |
| 4,181,621 | 1/1980 | Raaf et al. | 252/102 |
| 4,511,486 | 4/1985 | Shah | 134/42 |
| 4,540,504 | 9/1985 | Eoga | 252/99 |

FOREIGN PATENT DOCUMENTS 165145 6/1983 South Africa .

OTHER PUBLICATIONS

Skinner, E. W., and Phillips, R. W., *The Science of Dental Materials*, 6th edition, W. B. Saunders Co., Phila. and London, ©1967, pp. 200-201.

*Primary Examiner*—Asok Pal
*Attorney, Agent, or Firm*—Daniel A. Scola, Jr.; Henry C. Jeanette; Gary M. Nath

[57] ABSTRACT

A sprayable liquid denture cleanser composition comprising an aqueous solution of a detergent selected from the group consisting of sulfonated, sulfated and sulfoacetate fatty alcohols, and a chelating agent of the amino carboxylate or organo phosphonate type. The cleanser is preferably dispensed from a mechanical non-aerosol spraying device such that the force of the spray supplements the cleansing effect of the composition. The composition has particular application on the removal of tartar and calculus as well as stains and plaque adhering thereto.

20 Claims, 2 Drawing Figures

FOOD STAIN

TILES: COFFEE, TEA, BLUEBERRY AND GRAPE.

PRIOR ART 1

INVENTIVE COMPOSITION

PRIOR ART 2

TOBACCO AND FOOD STAIN
TILES: COFFEE, TEA,
BLUEBERRY AND GRAPE
ON PLAQUE MATRIX

INVENTION
COMPOSITION

PRIOR ART 2

LIQUID DENTURE CLEANSER COMPOSITION AND METHOD OF APPLICATION

This application is a continuation-in-part of co-pending U.S. Ser. No. 684,818, filed Dec. 20, 1984, now abandoned.

The instant invention relates to a liquid cleanser composition comprising (a) a detergent selected from the group consisting of sulfated, sulfonated and sulfoacetate fatty alcohols; (b) a chelating agent of the amino carboxylate or organo phosphonate type; and (c) about 50% to about 94% water. The composition is designed to be delivered to the surface through a spray pump system or device. The inventive cleansers are particularly useful as denture cleansers.

The denture cleanser prior art has focused on the use of oxidizing agents and bleaching agents in concert to remove visible stain and scale or plaque buildup. For the most part these compositions have employed a variety of sulfate salts, e.g., bisulfates and monopersulfates, to serve as detergents and oxidizers, as well as alkali metal and alkali earth metal halides as bleaches. Perborate, carbonate, bicarbonate and phosphate salts were conventionally included to provide effervescence and activation. These references have focused on making powdered or tableted products which dissolve rapidly and effervesce when placed in water. These products clean dentures generally in 12–30 minutes or longer and require constant emersion during this period, followed by brushing and rinsing with water.

The persulfate and perborate systems of the prior art tend to discolor the stain on the denture. Tablets made from these ingredients were limited to small amounts of detergents or surfactants in order to achieve fast dissolution and subsequent cleansing when placed in water. Detergents of the high fatty alcohol type could therefore not be incorporated except in minute quantities, e.g., 1% or less, or poor tablet dissolution rates resulted. The use of hypochlorites as bleaching agents discolor denture stain to an even greater extent then the persulfates and perborates. These chlorinated agents have a more serious disadvantage in that they produce an intolerable and unpleasant after taste and odor and may adversely discolor denture metal under certain conditions.

Additionally, althouth the prior art powder and tablet systems remove some of the denture stain, they tend to leave an undissolved residue which can only be removed mechanically. Consumers usually revert to a soaking and brushing regimen to obtain a thoroughly clean denture. Other types of undissolved residue include chewing gum residue and denture adhesive residue. These residues are particularly difficult to remove even with a regular brushing regimen since they become imbedded in the dentures or partial dentures. This obviously has adverse effects on the denture wearer. Even those chewing gums having non-stick properties and specially formulated for denture wearers become to some extent imbedded in the denture crevices. Denture wearers generally prefer a strong denture adhesive to insure proper adhesive of the denture in the mouth. These types of adhesives have the disadvantage of being very difficult to remove and clean from the denture. The use of water in combination with denture cleanser pastes tend to spread out rather than remove the chewing gum and adhesive residue and therefore fail to clean them from the denture surface. The inventive compositions solve this problem by lossening the chewing gum and adhesive residue such that it can then be removed with gentile rubbing with the fingers.

More recently a liquid denture cleanser has been disclosed in U.S. Pat. No. 4,511,486. This reference discloses a foam-producing liquid composition comprising from about 1 to about 10% by weight of a pharmaceutically acceptable surfactant, about 35 to about 70% by weight of ethanol or isopropanol or mixtures thereof, about 0.1 to about 10% by weight of a pharmaceutically acceptable humectant, about 25 to about 60% water and about 0.5% of an adjuvant. The composition must not contain more than 50% water when 42% alcohol is present and vice versa. Those surfactants disclosed are sodium lauryl sulfate SLS, sodium dodecyl benzene sulfonates SDBS, polysorbate 80, poloxomer 407 and mixtures thereof. Humectants are selected from the group consisting of glycerin, sorbitol, polyethylene glycol PEG, propylene glycol PG and mixtures thereof. The use of the trisodium salt of ethylene diamine tetracetic acid (EDTA) in an amount of about 0.5% is also disclosed as a useful adjuvant.

The composition of this reference relay on their high alcohol content for cleaning. As described hereinafter, comparative tests between the composition of this reference and the instant invention clearly demonstrate that the compositions of the instant invention are significantly better at removing plaque, calculus, tartar and stains from denture tiles, as well as actual dentures.

FIGS. I and II are photographs of stained dentures. These pictures clearly demonstrate the superior cleaning efficacy of the inventive liquid spray denture compositions over the prior art tableted composition as well as the prior art liquid denture cleanser of U.S. Pat. No. 4,511,486 described above.

The inventive liquid compositions are designed to be dispensed from a pump spray bottle. Thus, the viscosity of the compositions should be kept within a range which is atomizable or sprayable. The spray is effectuated without aerosol ingredients or pressurized means. The compositions do not use oxidizing agents or chlorine-containing compounds and consequently do not suffer from the disadvantages associated with these agents, as does the prior art. The liquid cleanser is sprayed onto the denture, allowed to stand for about 20 to about 120 seconds and rinsed in tap water. The length of time the cleanser is permitted to remain on the denture is dictated by the type and intensity of stain. Most food, tobacco and plaque stains, however, are easily removed after about 2 minutes of contact with the liquid cleanser. The inventive compositions are particularly effective at removing the calculus and tartar buildup. The instant invention has been shown to be effective in vivo, i.e., on actual dentures, in removing this buildup. If the composition is used regularly, e.g., on a daily basis, very little buildup of stubborn calculus or tartar results. When buildup has occurred on the denture, longer contact time between the cleanser and the denture is required. In such a case, even soaking for a short time might be recommended. The force of the pump spray supplements the cleansing effect of the cleanser. The pump spray force is designed to maximize the removal of food particles and stain on the denture surface. Thus, a minimum spray force is required such that it provides a mechanical cleansing action without a separate brushing step. The maximum force must be kept within a range which is controllable and convenient for the user. This is dictated primarily by consumer acceptability and marketing considerations.

An alternative embodiment to delivery via a pump spray device, is the use of the composition as a soaking solution. In this embodiment, it is suggested that the solution be diluted with water, since it is in a concentrated form.

More particularly, the instant liquid denture cleansing compositions consist essentially of (a) detergent present in amounts of about 3 to about 18% by weight selected from the group consisting of sulfonate fatty alcohols having the formula $RO-SO_3M$, sulfated fatty alcohols having the formula $ROSO_4M$, sulfoacetates having the formula $RO-COCH_2SO_3M$ and mixtures thereof, wherein R is $C_{10-16}$, M is a water soluble alkali metal or alkaline earth metal; and (b) a chelating agent present in amounts of about 3 to about 18% by weight selected from the group consisting of amino carboxylates, organo phosphonates and mixtures thereof; and (c) water present in amounts of about 50 to about 94% by weight.

The detergent is preferably used in the range of about 3 to about 12% and most preferably about 7 to about 10% by weight. As can be appreciated, the precise amounts chosen within these ranges will be dictated by the degree and type of stain present.

Preferred ranges of the chelating agent are from about 3 to about 15% by weight and more preferred about 3% to about 8% by weight.

When used in the preferred embodiment, e.g., the sprayable form, the weight ratio of detergent to chelating agent is about 2:1 to about 1:1. If the liquid concentrate is used alternatively as a soaking solution, the ratio is generally about 1:4 to about 1:2.

The use of sulfated higher fatty alcohols as detergents are well known. Such anionic detergents, however, when mixed with a suitable chelating agent, have surprisingly provided a highly effective denture cleanser which, when applied with the application force of a pump spray, provide a more convenient and efficient denture cleanser that the prior art methods. The user is able to clean his dentures without soaking them, as required in the prior art tablet and powder compositions, and without scrubbing or brushing, as required by the prior are sprayable compositions.

It is critical to the invention that the sulfated fatty alcohol detergent be used in conjunction with the recited chelating agents in aqueous solution. Certain of the useful detergents, e.g., sodium lauryl sulfate, when used by themselves and dispensed from a mechanical spraying device or from an aerosol mixture, produce an intolerable atmospheric condition situation which is harmful to the respiratory tract. Uncontrollable sneezing or coughing and respiratory irritation results. Such a situation would restrict the use to well ventilated, controlled areas. It has been discovered, quite unexpectedly, that the inventive compositions can be atomized or sprayed without these harmful side effects, by forming an aqueous mixture of the detergent with the amino carboxylate or organo phosphonate chelating agent. This combination helps alleviate the adverse respiratory and inhalation problems associated with the detergents and increases the cleaning efficacy of the composition. The weight ratio of detergent to chelator recited above has been carefully selected to achieve superior cleaning and to prevent the dispersion of irritating or harmful fumes.

Examples of useful sulfated fatty alcohol detergents are selected from the anionic water soluble class. The potassium, sodium and ammonium salts of the higher alkyl benzene sulfonates are preferred. Among these, the sodium linear alkyl benezene sulfonates are preferred. Other examples include magnesium lauryl sulfate, potassium lauryl sulfate, sodium dodecylbenzene sulfonate, sodium sulfoacetate, sodium myristyl sulfate, sodium lauryl sulfate, sodium cetyl sulfate, sodiun tridecyl sulfate and sodium-7-ethyl-2-methyl-4-undecyl sulfate. Mixtures of any and all of these detergents are also useful.

Other anionic detergents may be incorporated into the composition along with the above required detergnets. These supplemental detergents may be present in amounts of about 1 to about 5%. These additional detergents include compounds such as the oleic acid ester of sodium isethionate, sodium N-cyclohexyl-N-palmitoyl taurate, sodium N-coconut acid-N-methyl taurate, sodium N-methyl-N-oleyl taurate and mixtures thereof. Fluorochemical surfactants, commonly known as fluorads, are also useful additives. Examples include those compounds disclosed in British Pat. No. 1,322,548, having the formula:

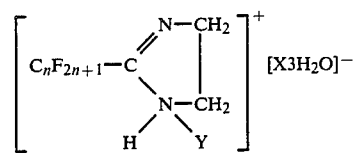

wherein n is an integer from 3 to 10, X is bromine or iodine; and Y is a glycol residue having 3 to 10 carbons derived, for example, from ethylene glycol or propylene glycol as a ethyoxylated alcohol having 1 to 10 moles of ethylene or propylene oxide.

The use of chelating or sequestering agents in the prior art was typically in combination with denture cleanser tablets containing peroxygen bleaching agents. The tetrasodium salt of ethylenediamine tetracetic acid ($Na_4EDTA$), among others, was commonly used to sequester the heavy metal impurities present in solution and prevent the decomposition of the bleaching agent.

Typically, denture cleansing tablets or powders have used chelating agents such as $Na_4EDTA$ in amounts of about 0.5%. More recently a denture tablet composition was described in U.S. Pat. No. 4,540,504 to Eoga, whereby from about 10 to about 50% by weight of chelator is present. These prior art references are solid tablet compositions, however, not solutions as in the instant invention. Thus, when the tablets are dissolved in water, and the relative amounts of ingredients are based on the weight of the solution, the chelator range is very small. For example, if the chelator range of tablet of the above-mentioned U.S. Pat. No. 4,540,504 patent is measured based on a weight of the solution it forms when dropped in 125 ml of water, the range is from about 0.16% to about 0.8% by weight. If a typical commercial tablet containing 0.5% $Na_4EDTA$ is dissolved in 125 ml of water, the chelating concentration based on the then formed solution is 0.012%. These amounts are much smaller than Applicant's range of about 3 to about 18% by weight.

Additional useful amino carboxylate chelators include tetrasodium ethylenediaminetetraacetate dihydrate, trisodium ethylenediaminetetraacetate, diammonium ethylenediaminetetraacetate, disodium ethylenediaminetetracetate dihydrate, trisodium N-hydroxyethylenediaminetriacetate hydrate trisodium nitrilotriacetate monohydrate, pentasodium diethylenetriaminepentaacetate, trisodium ethylenediaminetetraacetate trihydrate and mixtures thereof. These chelators, as well as other well known amino carboyxlates are generally used within the above-cited ranges in amounts sufficient to contribute to removal of calculus, tartar and any stain and plaque contained thereon.

Those organic phosphonates useful may be selected from a wide range of conventional materials. Examples include 1-hydroxy-1,1-diphosphonic acid and its sodium, potassium and ammonium salts. These salts are also sold under the tradename Dequest by Monsanto Company. In addition to being chelating agents, the organic phosphonates serve as detergent builders. These chelating agents are employed in the same amounts as the amino carboxylates. Mixtures of any and all of the chelators is also contemplated.

The inventive liquid denture cleansers can optionally contain detergent builders which are conventionally used in detergent formulations and which enhance cleaning and contribute to a brighter surface appearance of the denture. Useful builders include the water-soluble phosphates, pyrophosphates, ortho phosphates, carbonates and the like. Specific examples of inorganic phosphate builders useful include the sodium or potassium salts of tripolyphosphates, pyrophosphates and hexametaphosphates. These builders may also contribute to cleaning. As mentioned above, the organic phosphonate chelating agents also serve as builders. When incorporated into the composition, builders are generally present in amounts of about 3% to about 12%; and preferably in amounts of about 5% to about 10%.

Other conventional additives such as flavorings, colorants, perfumes, antimicrobials, preservatives, and the like may be optionally incorporated in the inventive compositions. For example, flavorings such as mint, oil of clove, artificial vanilla, to name a few, are useful. These materials may be blended in various combinations and the amounts may be varied according to the perception desired.

In the instance where colorants are used, F.D. & C. and D. & C. dyes may be used. Lakes are generally not useful due to their insolubility in the inventive compositions. Those dyes useful are certified by the Federal Food & Drug Administration as acceptable for use in food, drug and cosmetic applications and in drug and cosmetic colorings. The materials acceptable for the foregoing are preferably water-soluble and include F.D. & C. Blue No. 2 (indigo dye), F.D. & C. Green No. 1 and 3, to name a few. Conventional preservatives such as methyl and propyl paraben and mixtures thereof may be incorporated in amounts well known in the art.

As previously mentioned, the inventive liquid denture, cleanser compositions are designed to be applied to the denture surface from a mechanical spraying device. Simple hand spray pump bottles capable of disposing high viscosity fluids are sufficient. Aerosols, including piston-driven types, are also useful, but are not preferred since they are more costly and do not afford any advantages over the mechanical devices for purposes of this invention. Application by spraying imparts a certain mechanical cleaning force as the liquid hits the denture surface. By directing the spraying parameters, e.g., the spray pattern, the weight of liquid applied and the speed of the spray, the cleaning force can be controlled.

In measuring the force, one fluid once propylene cylindrical pump bottles having a high viscosity spray dispensing head were filled with the inventive compositions. The denture or other target was held stationery in an Instron tensile testing machine. The spray bottle was mounted horizontally above the target with the spray nozzle at a distance of 1" (2.54 cm) away. An air driven piston/solenoid device was used to actuate the spray pump. The air pressure driving the piston was approximately 5 psi (0.35 kg/cm$^2$). The peak force of the spray against the target was recorded by a microprocessor connected to the Instron load cell's output. The measurement was in gram force units. The results indicated that a gram force of at least 1 and preferably between about 1 to 3 is required to provide enough mechanical action to supplement the cleaning effect of the composition itself.

The weight of the liquid dispensed per actuation of the mechanical spraying device was measured by subtracting the weight of the liquid and spray bottle after dispensation with the weight prior to dispensation.

The average weight delivered per actuation is about 90 to about 200 mg of liquid; and preferably about 100 to about 150 mg±25 mg of liquid. These amounts are preferred for adequate cleaning of most stains and plaque.

The spray pattern v as determined by stationing the spray pump bottle and directing the spray nozzle onto an absorbant pad situated about 2" (5 cm) away. The pump sprayer was actuated once and the vertical and horizontal diameters of the spray pattern were measured as they appeared on the pad. The spray pattern is preferably about 1.5" (3.81 cm) to about 2.5" (6.35 cm) by 1.5" (3.81 cm) to about 2.5" (6.35 cm) at a distance of about 2" (5 cm) from the target. Most preferably, the spray pattern is about 1.85" (4.6 cm)±0.65" (1.65 cm)×1.85 (4.6 cm)±0.65" (1.65 cm) at the 2" (5 cm) distance from the target.

The above measurements were taken to obtain the minimum parameters related to the mechanical force required to achieve cleaning. While the composition itself is a good cleanser, surprisingly improved cleaning of the denture is achieved when the composition is sprayed with sufficient mechanical force to help remove stain, plaque and other debris.

Additional considerations must be given to the choice of detergent/chelator formulation such that the formation of undesirable precipitates is minimized and to prevent the liquid's viscosity from becoming so high that dispensing from a spray bottle is difficult. For example, when ethylenediamine tetracetic tetrasodium salt is used in conjunction with sodium lauryl sulfoacetate (Lanthanol LAL) or another linear alkyl sulfonates, the detergent tends to salt out, forming an insoluble precipitate and resulting in a thick unsprayable mass. Additionally, the cleansing efficacy of the composition is deleteriously affected when such precipitates form. Thus, it is important that the chelators be readily water-soluble and that the combination of the chelator and detergent result in a solution whose viscosity is readily and easily dispensed from a mechanical spraying device, and whose stability is maintained during storage. The viscosity problems and the salting-out effect generally occur at concentrations of chelator above 5% and at temperatures below room temperature. Once the insoluble precipitate is formed it is very difficult to reverse. To help alleviate these problems, agents which depress the freezing point and prevent the formation of insoluble precipitate can be added. Water soluble, not-toxic glycols, such as polyethylene glycols, in an amount sufficient to prevent an insoluble precipitate from forming are particularly useful in addressing this problem. The addition of these materials in amounts of from about 1 to about 10% by weight help maintain a stable liquid solution during storage or shelf-life. Examples of preferred polyethylene glycols are those having an average molecular weight range of about 200 to about 600. These materials are sold under the tradename Carbowax by Union Carbide, Danbury, CT. Other non-toxic, water-soluble derivations of the polyethylene glycols, e.g., alkoxy or ether derivatives are also contemplated.

The term "denture" as used herein, includes artificial teeth, removable orthodontic bridges, dentures, plates and the like.

A high degree of cleansing is generally achieved in less than 1 minute and preferably in 30 seconds or less. The cleansers, with the aid of the mechanical force exerted by the spray, strip off calculus, tartar and plaque, remove mucous resulting from the depositions of proteins and glycoproteins, remove food particles and debris, remove and/or kill bacteria, remove residual denture adhesives and chewing gum, and remove food stains and tobacco stains as well as coffee and tea stains. These compositions have been shown to effectively loosen chewing gum and denture adhesive such that these residues can be easily removed by gently rubbing with the fingers or gentle brushing. These cleansing effects are achieved without adversely affecting the metal, plastic or other materials of the denture construction.

The instant invention allows the denture wearer to clean his dentures quickly, conveniently in a portable package without the need for a container for soaking.

A fuller understanding of the present invention will be gained from the following illustrative examples. Unless specified otherwise all amounts expressed as percent are intended to be a percent by weight of the total composition.

EXAMPLE ONE

Denture Cleanser compositions were prepared using the formulations tabulated below. Compositions A and B represent preferred embodiments of the inventive liquid denture spray composition. Compositions C and D represent commercially available denture tablets.

| Ingredients | A Inventive (Liquid) | B Inventive (Liquid) | C (Prior/art tablet) | D (Prior/art tablet) |
|---|---|---|---|---|
| Sodium Dodecyl Benzene Sulfonate | — | 10 | — | — |
| Sodium Lauryl Sulfate | 10% | — | — | — |
| Ethylenediaminetetraacetic Acid Tetrasodium Salt | 5% | 5 | 3.4 | 1.25 |
| Polyethylene Glycol | — | 4 | — | — |
| Flavor, color, preservative | 0.5% | 0.5 | — | — |
| Water | 85.5% | 80.5 | — | — |
| Sodium Bicarbonate | — | — | — | 14.0 |
| Citric Acid | — | — | — | 10.3 |
| Sodium Carbonate | — | — | — | 12.8 |
| Colorant | — | — | 0.2 | 0.1 |
| Oxone | — | — | — | 39.5 |
| Flavor and Fragrance | — | — | 0.5 | 1.0 |
| Detergent | — | — | 0.5 | 0.65 |
| Magnesium Stearate | — | — | — | 0.2 |
| Sodium Perborate Monohydrate | — | — | 37.3* | 12.5 |
| Anhydrous Sodium Perborate | — | — | 22.85* | — |
| Trisodium Phosphate | — | — | 33.8 | — |
| Sodium Benzoate | — | — | 1.0 | 1.6 |
| Polytetrafluoroethylene | — | — | 0.45 | — |
| Filler | — | — | — | 6.1 |

*Includes approximately 0.45% by weight of total perborate polytetrafluoroethylene prepared as a granulated mixture.

In vitro denture tiles were prepared with plague, a composite of food stain consisting of grapes, blueberry, tea and coffee as well as tobacco stain.

Samples of the tiles were then chosen to be cleansed with one of the three compositions listed above. The treatment with Compositions A & B (inventive) were accomplished by spraying the tiles and allowing the spray to remain on each tile type for 30, 60 and 120 seconds prior to rinsing with water at 45° C. for 20 seconds.

The treatment with the tablets of Composition C and D (prior art) was accomplished by dropping the tablets in beakers of 45° C. water containing the tiles. Those tiles treated with Composition C were allowed to soak for 5 minutes. Those tiles treated with Composition D were allowed to soak for 12 minutes.

The results showed that tiles cleaned by the inventive Compositions A and B for 120 seconds were significantly cleaner than those cleaned with Composition C and D.

Those denture tiles which were cleaned with the inventive Compositions A and B for 30 and 60 seconds required an additional spraying and an immediate rinsing in order to achieve similar results to the 120 second treatment.

Those tiles which had 24 hours plaque accumulated on them were sprayed with Compositions A and B and allowed to stand for 12 minutes. Additional plaque tiles were soaked in Compositions C and D for 5 and 12 minutes respectfully. All the tiles were then rinsed under running water at 45° C. for 20 seconds and immersed in a basic 0.01% Fuchsin solution. The Fuchsin solution is used as a color indicator for plaque and calculus. The tiles were the rinsed again ad qualitatively compared for red color. The tiles cleaned with Compositions A & B (inventive) had the least amount of red color resulting from the Fuchsin, and consequently the least amount of plaque.

EXAMPLE TWO

This example is intended to show a comparison between the cleansing efficacy of inventive compositions as compared to a well known commercial tablet of the prior art and the liquid foaming denture cleanser disclosed in U.S. Pat. No. 4,511,486) Composition C.

A set of tiles (Set I) were prepared with coffee, tea, blueberry and grape stains. Another set (Set II) of tiles were prepared having tobacco, coffee, tea, blueberry and grape on a plaque matrix.

FIG. I shows the results of the food stained tiles after cleaning with each of the denture cleansers. "Prior Art I," as labeled in the Figures, is the commercial tableted denture cleanser (Composition D, Example One), which was dissolved in a beaker of water (45° C.) containing the tile and left for 12 minutes.

The "Inventive Composition," as labeled in the Figures, is formulation A set forth in Example 1. The spray was left on the tile for 120 seconds and rinsed with water for 20 seconds at 45° C.

"Prior Art II," as labeled in the Figures, is the liquid foaming Composition C set forth in U.S. Pat. No. 4,511,486. The chelator EDTA has been added for the sake of comparison to the instant inventive compositions. This composition had the following formula:

| | |
|---|---|
| Sodium dodecyl benzene sulfonate | 3% |
| Polysorbate 80 | 1% |
| Glycerin | 1.5% |
| PEG 400 | 0.5% |
| Ethyl alcohol | 55% |
| Water | 36.75% |
| Flavor/color | 1.75% |
| EDTA | 0.5% |

From observing the photographs in FIGS. I and II, the cleaner (whiter) surfaces are those cleansed with the inventive compositions. Those tiles cleaned with the compositon of U.S. Pat. No. 4,511,486 did not become clean and therefore exhibit a dark color. These pictures were taken under identical conditions, and accurately reflect the actual appearance after cleaning. It is apparent that the inventive liquid spray denture cleanser compositions exhibited significantly better cleaning than the prior art tableted denture cleanser and the prior art liquid denture cleansers.

EXAMPLE THREE

Further tests were conducted for the purpose of comparing inventive liquid denture spray composition with those compositions disclosed in U.S. Pat. No. 4,511,486, particularly with respect to their abilities to clean visible tartar and calculus deposits without brushing. Additionally, a preliminary experiment was conducted for the purpose of comparing the respective abilities of the compositions to dissolve hydroxyapatite, the main ingredient found in tartar and calculus deposits. Hydroxyapatite is a major type of calcium phosphate responsible for calculus and tartar deposits. (Schroeder, H.E., *Formation & Inhibition of Dental Calculus*, Hans Huber Publishers, p 117-119, 1969).

Five denture cleaning solutions were prepared in accordance with the following compositions:

| Ingredient | Inventive A | (U.S. Pat. No. 4,511,486) | | | | Control F |
|---|---|---|---|---|---|---|
| | | B | C | D | E | |
| Sodium Lauryl Sulfate | 10.0 | 5.0 | 5.0 | 5.0 | 5.0 | — |
| Na4 EDTA | 5.0 | — | — | — | — | — |
| Na3 EDTA | — | 0.5 | 0.5 | — | 0.5 | — |
| Glycerin | — | 1.0 | 1.0 | 1.0 | 1.0 | — |
| Methylparaben | 0.1 | — | — | — | — | — |
| Propylparaben | 0.05 | — | — | — | — | — |
| Polyethylene Glycol E400 | 1.0 | — | — | — | — | — |
| 95% Alcohol | — | 30 | 47.0 | 47.0 | 42.0 | — |
| Water | 52.05 | 63.5 | 46.5 | 47.5 | 46.5 | 100.0 |

Composition A represents an embodiment of the present invention. Compositions B-E represent compositions of U.S. Pat. No. 4,511,486. The control formulation (F) was ordinary tap water.

Hydroxyapatite Dissolution Tests

Prior to testing the cleaning efficacy of the compositions on tartar and calculus, a preliminary test was conducted to determine the effectiveness of the compositions in dissolving hydroxyapatite (HA), a compound known to be a common type of calculus. To each of the above solution compositions was added powdered hydroxyapatite (HA), the known main ingredient found in tartar and calculus deposits. To 50 ml of the Inventive Composition (A) was added 100 mg of HA. To 100 ml of each of Compositions B-F was added 100 mg of HA. The concentration of HA in the Inventive Compositions (A) was twice that of the prior art (B-F) to emphasize the greater ability of the Inventive Compositions at dissolving HA (calculus).

At the end of two hours of soaking the Inventive Compositions (A) had completely dissolved the HA and the solution remained clear even after one (1) week at room temperature. The prior art and control solutions, however, exhibited cloudy solutions after one (1) week of soaking, indicating failure of these compositions to dissolve the HA. Composition B, which had the least amount of alcohol present relative to compositions C-E, exhibited less cloudiness than the others.

Actual Denture Tests

At this point actual dentures were obtained, having visible buildup of tartar and calculus stain and deposits, from subjects. The dentures had not been exposed to any pretreatment whatsoever, nor were the subjects on any special oral hygiene program. The tartar and calculus stains and deposits represented buildup occurring during ordinary usage and hygiene. Photographs of the dentures clearly indicated the buildup.

A denture was selected which was evenly stained with tartar and calculus deposits on both the right and left sides. The denture was first photographed, then rinsed under running water and subjected to the following regimen.

The left side of the denture was soaked in U.S. Pat. No. 4,511,486 Composition B for four (4) hours at room temperature. The denture was the rinsed, air dried and photograhed. No visible stain difference was detectable between the side which was treated and untreated side, indicating that no significant removal of the tartar and calculus deposits occurred.

The right side of the same denture was then soaked in the Inventive Composition (A) for one (1) hour at room temperature. The denture was then rinsed, air dried and photographed. The result was that no visible detectable tartar or calculus deposit remained, indicating that the deposits were removed from the denture.

The above experiments indicate the following:

(1) The inventive composition are able to dissolve hydroxyapatite, the main constituent in calculus and tartar, while the prior art compositions of U.S. Pat. No. 4,511,486 are not.

(2) The inventive compositions are capable of removing stubborn calculus and tartar deposits and stain on dentures in one (1) hour of soaking, without brushing or other mechanical action. The compositions of U.S. Pat. No. 4,511,486 did not visibly show any removal of the deposits even after four (4) hours of soaking.

It is therefore evident, in view of this experiment that the inventive denture spray compositions exhibit surprisingly superior results over U.S. Pat. No. 4,511,486.

EXAMPLE FOUR

The following compositions were prepared as a means of demonstrating some of the various combinations possible within the ranges claimed. Those solutions which remained clear during storage are considered preferred embodiments since they remained free of precipitate and were therefore easier to dispense through a spray nozzle. Additionally, those solutions which remained free of precipitate maintained the availability of the total detergent for cleaning. The balancing of the ingredients within the preferred ranges such that adequate cleaning and sprayability exist, without excessive precipitate, is within the scope of routine experimentation.

| Composition | % by weight | | | | | | Clear/ppt |
|---|---|---|---|---|---|---|---|
| | SLS | SDBS | EDTA | Phosphonate | PEG | PG | |
| 1 | 15 | — | 18 | — | — | — | ppt |
| 2 | 15 | — | 18 | — | 10 | — | Slight ppt |
| 3 | 5 | — | 10 | — | — | — | ppt |
| 4 | 5 | — | 10 | — | 4 | — | Clear |
| 5 | 5 | — | 10 | — | 6 | — | Clear |
| 6 | 3 | — | 5 | — | 0 | — | ppt |
| 7 | 10 | — | 5 | — | 4 | — | Clear |
| 8 | 3 | — | 5 | — | 2 | — | Clear |
| 9 | 3 | — | 3 | — | 0 | — | Clear |
| 10 | 3 | — | 3 | — | 2 | — | Clear |
| 11 | 15 | — | 18 | — | — | 0 | ppt |
| 12 | 15 | — | 18 | — | — | 10 | ppt |
| 13 | 5 | — | 10 | — | — | 0 | ppt |
| 14 | 5 | — | 10 | — | — | 4 | ppt |
| 15 | 5 | — | 10 | — | — | 6 | ppt |
| 16 | 5 | — | 10 | — | — | 8 | Clear |
| 17 | 3 | — | 5 | — | — | 0 | ppt |
| 18 | 10 | — | 5 | — | — | 4 | Clear |
| 19 | 3 | — | 5 | — | — | 2 | Clear |
| 20 | 3 | — | 3 | — | — | 0 | Clear |
| 21 | 3 | — | 3 | — | — | 2 | Clear |
| 22 | — | 18 | 18 | — | 0 | — | ppt |
| 23 | — | 18 | 18 | — | 10 | — | ppt |
| 24 | — | 5 | 10 | — | 0 | — | ppt |
| 25 | — | 5 | 10 | — | 4 | — | ppt |
| 26 | — | 5 | 10 | — | 6 | — | Clear |
| 27 | — | 3 | 5 | — | 0 | — | ppt |
| 28 | — | 10 | 5 | — | 4.5 | — | Clear |
| 29 | — | 3 | 5 | — | 2 | — | Clear |
| 30 | — | 3 | 3 | — | 0 | — | Slight ppt |
| 31 | — | 3 | 3 | — | 2 | — | Clear |
| 32 | — | 10 | 5 | — | 4 | — | Clear |
| 33 | — | 18 | 18 | — | 0 | — | ppt |
| 34 | — | 18 | 18 | — | — | 10 | ppt |
| 35 | — | 5 | 10 | — | — | 0 | ppt |
| 36 | — | 5 | 10 | — | — | 4 | ppt |
| 37 | — | 5 | 10 | — | — | 6 | Clear |
| 38 | — | 3 | 5 | — | — | 0 | ppt |
| 39 | — | 10 | 5 | — | — | 4 | Clear |
| 40 | — | 3 | 5 | — | — | 2 | Clear |
| 41 | — | 3 | 3 | — | — | 0 | Clear |
| 42 | — | 3 | 3 | — | — | 2 | Clear |
| 43 | — | 15 | — | 16 | 0 | — | ppt |
| 44 | — | 15 | — | 16 | 10 | — | Light ppt |
| 45 | — | 5 | — | 10 | 0 | — | ppt |
| 46 | — | 5 | — | 10 | 4 | — | Clear |
| 47 | — | 5 | — | 10 | 6 | — | Clear |
| 48 | — | 5 | — | 10 | 8 | — | Clear |
| 49 | — | 3 | — | 5 | 0 | — | ppt |
| 50 | — | 10 | — | 5 | 4 | — | Clear |
| 51 | — | 3 | — | 5 | 2 | — | Clear |
| 52 | — | 3 | — | 3 | 0 | — | ppt |
| 53 | — | 3 | — | 3 | 2 | — | Clear |
| 54 | — | 15 | — | 16 | — | 0 | ppt |
| 55 | — | 15 | — | 16 | — | 10 | ppt |
| 56 | — | 5 | — | 10 | — | 0 | ppt |
| 57 | — | 5 | — | 10 | — | 4 | ppt |
| 58 | — | 5 | — | 10 | — | 6 | ppt |
| 59 | — | 5 | — | 10 | — | 8 | ppt |
| 60 | — | 3 | — | 5 | — | 0 | ppt |
| 61 | — | 10 | — | 5 | — | 4 | ppt |
| 62 | — | 3 | — | 5 | — | 2 | ppt |
| 63 | — | 3 | — | 3 | — | 0 | ppt |
| 64 | — | 3 | — | 3 | — | 2 | ppt |
| 65 | — | 3 | — | 5 | — | 4 | ppt |
| 66 | — | 3 | — | 5 | — | 6 | ppt |
| 67 | 15 | — | — | 16 | 0 | — | ppt |
| 68 | 15 | — | — | 16 | 10 | — | ppt |
| 69 | 5 | — | — | 10 | 0 | — | ppt |
| 70 | 5 | — | — | 10 | 4 | — | ppt |
| 71 | 5 | — | — | 10 | 6 | — | ppt |
| 72 | 5 | — | — | 10 | 8 | — | ppt |
| 73 | 3 | — | — | 5 | 0 | — | ppt |
| 74 | 10 | — | — | 5 | 4 | — | ppt |
| 75 | 3 | — | — | 5 | 2 | — | ppt |
| 76 | 3 | — | — | 3 | 0 | — | ppt |
| 77 | 3 | — | — | 3 | 2 | — | ppt |
| 78 | 3 | — | — | 3 | 6 | — | ppt |
| 79 | 3 | — | — | 3 | 10 | — | ppt |
| 80 | 1.5 | — | — | 1.5 | 5 | — | ppt |
| 81 | 15 | — | — | 16 | — | 0 | ppt |
| 82 | 15 | — | — | 16 | — | 10 | ppt |
| 83 | 5 | — | — | 10 | — | 0 | ppt |
| 84 | 5 | — | — | 10 | — | 4 | ppt |
| 85 | 5 | — | — | 10 | — | 6 | ppt |
| 86 | 5 | — | — | 10 | — | 8 | ppt |
| 87 | 3 | — | — | 5 | — | 0 | ppt |
| 88 | 10 | — | — | 5 | — | 4 | ppt |
| 89 | 3 | — | — | 5 | — | 2 | ppt |
| 90 | 3 | — | — | 3 | — | 0 | ppt |
| 91 | 3 | — | — | 3 | — | 2 | ppt |
| 92 | 3 | — | — | 3 | — | 6 | ppt |
| 93 | 3 | — | — | 3 | — | 10 | ppt |
| 94 | 1.5 | — | — | 1.5 | — | 5 | ppt |

This invention may be embodied in other forms or carried out in other ways without departing from the spirit or essential characteristics thereof. The present disclosure is therefore to be considered as illustrative and not restrictive, the scope of the invention being indicated by the appended claims. All modifications which come within the meaning and range of equivalency are intended to be embraced herein.

What is claimed is:

1. A storage stable liquid denture cleanser composition consisting essentially of
   (a) a detergent present in amounts of about 3 to about 18% by weight selected from the group consisting of sulfonate fatty alcohols having the formula RO-$SO_3M$, sulfated fatty alcohols having the formula $ROSO_4M$, sulfoacetates having the formula RO-$COCH_2SO_3M$ and mixtures thereof, wherein R is $C_{10-16}$, M is a water soluble alkali metal or alkaline earth metal; and
   (b) a water-soluble chelating agent present in amounts of about 3 to about 18% by weight selected from the group consisting of amino carboxylate, organo phosphonates and mixtures thereof; and (c) water present in amounts of about 50 to about 94% by weight.

2. The cleanser of claim 1 wherein the fatty alcohol detergent is selected from the group consisting of potassium lauryl sulfate, magnesium lauryl sulfate, sodium lauryl sulfate, sodium cetyl sulfate, sodium tridecyl sulfate, sodium-7-ethyl-2-methyl-4-undecyl sulfate, sodium dodecylbenzene sulfonate, sodium lauryl sulfonacetate and mixtures thereof.

3. The cleanser of claim 1 wherein the chelating agent is selected from the group consisting of tetrasodium ethylenediaminetetraacetate dihydrate, trisodium ethylenediaminetetraacetate, diammonium ethylenediaminetetraacetate, sodium ethylenediaminetetraacetate dihydrate, trisodium N-hydroxyethylenediaminetriacetate hydrate, trisodium nitrilotriacetate monohydrate, pentasodium diethylenetriaminepentaacetate, trisodium ethylenediaminetetraacetate trihydrate, the sodium salt of 1-hydroxy-1,1-diphosphonic acid, the potassium salt of 1-hydroxy-1,1-disphosphonic acid, the amonium salt of 1-hydroxy-1,1-disphosphonic acid and mixtures thereof.

4. The cleanser of claim 1 wherein the cleanser is in sprayable form and wherein the ratio of detergent to chelating agent is about 2:1 to about 1:1.

5. The cleanser of claim 1 wherein the chelator is present in amounts of about 3% to about 8% by weight.

6. The cleanser of claim 1 wherein the detergent is present in amounts of about 3% to about 12%.

7. The cleanser of claim 1 wherein there is an additional anionic detergent selected from the group consisting of the oleic acid ester of sodium isethionate, sodium N-cyclohexyl-N-palmitoyl taurate, sodium N-coconut acid-N-methyl taurate, sodium N-methyl-N-oleyl taurate, fluorochemical surfactants having the formula $$\left[ C_nF_{2n+1}-C \underset{\underset{H}{\diagdown}}{\overset{\overset{N-CH_2}{\diagup\!\!\!\!\diagup}}{\diagup}} \underset{Y}{\overset{}{\diagdown}} N-CH_2 \right]^+ [X3H_2O]^-$$

wherein n is an integer from 3 to 10, X is bromine or iodine, and Y is a glycol residue having 3 to 10 carbons and mixtures thereof.

8. The cleanser of claim 1 wherein there is additionally present a material selected from the group consisting of flavorings, colorings, perfumes, preservatives, builders, antimicrobials and mixtures thereof.

9. The cleanser of claim 8 wherein the preservative is a paraben, the flavoring is mint and the builder is selected from the group consisting of water-soluble, phosphate, pyrophosphates, ortho phosphates, carbonates and mixtures thereof and the coloring is an F.D. & C. or D. &. C. dye.

10. The cleanser of claim 1 wherein the cleanser is a soaking solution and wherein the ratio of detergent to chelating agent is about 1:4 to about 1:2.

11. A method of cleansing dentures comprising:
(1) spraying the denture with a storage stable liquid denture spray composition consisting essentially of:
(a) a detergent present in amounts of about 3 to about 18% by weight selected from the group consisting of sulfonate fatty alcohols having the formula $ROSO_3M$, sulfated fatty alcohols having the formula $ROSO_4M$, sulfoacetates having the formula $ROCOCH_2SO_3M$ and mixtures thereof, wherein R is $C_{10-16}$, M is a water soluble alkali metal or alkaline earth metal; and
(b) a water-soluble chelating agent present in amounts of about 3 to about 18% by weight selected from the group consisting of amino carboxylates, organo phosphonates and mixtures thereof; and
(c) water present in amounts of about 50 to about 94% of weight; and
(2) rinsing the denture with water.

12. The method of claim 11 wherein the spray has a force of at least one gram.

13. The method of claim 11 wherein the spray has a pattern with at least about 1.5″ to about 2.5″ when sprayed from a distance of about 2″ from the denture.

14. The method of claim 11 wherein the liquid denture composition is allowed to remain on the denture for about 20 to about 120 seconds prior to rinsing with water.

15. A storage stable liquid denture cleanser composition consisting essentially of:
(a) a detergent present in amounts of about 3 to about 18% by weight selected from the group consisting of sulfonate fatty alcohols having the formula $ROSO_3M$, sulfated fatty alcohols having the formula $ROSO_4M$, sulfoacetates having the formula $ROCOCH_2SO_3M$ and mixtures thereof, wherein R is $C_{10-16}$, M is a water soluble alkali metal or alkaline earth metal; and
(b) a water-soluble chelating agent present in amounts of about 3 to about 18% by weight selected from the group consisting of amino carboxylate, organo phosphonates and mixtures thereof;
(c) water present in amounts of about 50 to about 94% by weight; and
(d) a water-soluble, non-toxic glycol in an amount sufficient to prevent an insoluble precipitate from forming.

16. The cleanser of claim 15 wherein said glycol is a polyethylene glycol.

17. The cleanser of claim 16 wherein the polyethylene glycol is present in amounts of about 1 to about 10% by weight.

18. The cleanser of claim 17 wherein the polyethylene glycol has an average molecular weight of about 200 to about 600.

19. The cleanser of claim 15 wherein the cleanser is in sprayable form and wherein the ratio of detergent to chelating agent is about 2:1 to about 1:1.

20. The cleanser of claim 15 wherein the cleanser is a soaking solution and wherein the ratio of detergent to chelating agent is about 1:4 to about 1:2.

* * * * *

UNITED STATES PATENT AND TRADEMARK OFFICE
CERTIFICATE OF CORRECTION

PATENT NO. : 4,701,223
DATED : October 20, 1987
INVENTOR(S) : Anthony B. J. Eoga It is certified that error appears in the above-identified patent and that said Letters Patent is hereby corrected as shown below:

In the Specification

Column 2, line 23, "relay" should read --rely--.

Column 3, line 10, before "detergent" insert --a--.

Column 3, line 44, "that" should read --than--.

Column 3, line 48, "are" should read --art--.

Column 5, line 6, after "hydrate" insert --,--.

Column 5, line 10, "carboyxlates" should read --carboxylates--.

Column 6, line 5, "once" should read --ounce--.

Column 7, line 5, "not-toxic" should read --non-toxic--.

Column 7, lin3 8, after the first occurence of "ing" and before "are", insert --,-- so that the word "forming" bridging lines 7 and 8 reads --forming,--.

Column 7, line 16, "derivations" should read --derivatives--.

Column 8, line 57, the second instance of "the" should read --then--.

Column 8, line 57, "ad" should read --and--.

UNITED STATES PATENT AND TRADEMARK OFFICE
CERTIFICATE OF CORRECTION

PATENT NO. : 4,701,223

DATED : October 20, 1987

INVENTOR(S) : Anthony B.J. Eoga

It is certified that error appears in the above-identified patent and that said Letters Patent is hereby corrected as shown below:

Column 8, the last line thereof, after "4,511,486" delete --)--.

Column 10, at line 12, "Hydroxyapatite Dissolution Tests" should read --<u>Hydroxyapatite Dissolution Tests</u>--.

Column 10, at about line 37, "Actual Denture Tests" should read --<u>Actual Denture Tests</u>--.

Column 10, line 53, the second instance of "the" should read --then--.

Signed and Sealed this

Tenth Day of May, 1988

Attest:

DONALD J. QUIGG

Attesting Officer

Commissioner of Patents and Trademarks